United States Patent
Safronov et al.

(10) Patent No.: US 10,059,599 B2
(45) Date of Patent: Aug. 28, 2018

(54) SYNTHESIS OF BORANE COMPOUNDS

(71) Applicants: Alexander Valentinovich Safronov, Columbia, MO (US); Satish Subray Jalisatgi, Columbia, MO (US); Marion Frederick Hawthorne, Columbia, MO (US)

(72) Inventors: Alexander Valentinovich Safronov, Columbia, MO (US); Satish Subray Jalisatgi, Columbia, MO (US); Marion Frederick Hawthorne, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 15/116,365

(22) PCT Filed: Feb. 3, 2015

(86) PCT No.: PCT/US2015/014224
§ 371 (c)(1),
(2) Date: Aug. 3, 2016

(87) PCT Pub. No.: WO2015/117119
PCT Pub. Date: Aug. 6, 2015

(65) Prior Publication Data
US 2016/0347621 A1    Dec. 1, 2016

Related U.S. Application Data

(60) Provisional application No. 61/965,689, filed on Feb. 3, 2014.

(51) Int. Cl.
| | |
|---|---|
| *C01B 35/10* | (2006.01) |
| *C01B 35/00* | (2006.01) |
| *C01B 35/14* | (2006.01) |
| *C01B 35/12* | (2006.01) |
| *C07F 5/02* | (2006.01) |
| *C07F 5/04* | (2006.01) |

(52) U.S. Cl.
CPC ............ *C01B 35/00* (2013.01); *C01B 35/121* (2013.01); *C01B 35/14* (2013.01); *C07F 5/022* (2013.01); *C07F 5/04* (2013.01)

(58) Field of Classification Search
CPC .......... C07F 5/022; C07F 5/04; C01B 35/026; C01B 35/00; C01B 35/14; C01B 35/121
See application file for complete search history.

(56) References Cited

U.S. PATENT DOCUMENTS

| | | | |
|---|---|---|---|
| 3,108,139 A | 10/1963 | Larchar, Sr. et al. | |
| 3,227,754 A | 1/1966 | Bragdon et al. | |
| 3,373,202 A | 3/1968 | Makhlouf et al. | |
| 3,373,203 A | 3/1968 | Makhlouf et al. | |
| 5,582,808 A | 12/1996 | Patek | |
| 6,086,837 A * | 7/2000 | Cowan .................. | C01B 35/026 423/294 |
| 7,524,477 B2 | 4/2009 | Spielvogel et al. | |
| 7,641,897 B2 | 1/2010 | Weissman et al. | |
| 7,718,154 B2 | 5/2010 | Ivanov et al. | |
| 2004/0249215 A1 | 12/2004 | Suda et al. | |
| 2005/0080048 A1 * | 4/2005 | Tavassoli ................ | C07F 5/025 514/64 |
| 2005/0169827 A1 | 8/2005 | Spielvogel et al. | |
| 2005/0169828 A1 | 8/2005 | Spielvogel et al. | |
| 2006/0286019 A1 * | 12/2006 | Ivanov .................... | C07F 5/022 423/277 |
| 2006/0286020 A1 | 12/2006 | Ivanov et al. | |

FOREIGN PATENT DOCUMENTS

| | | |
|---|---|---|
| FR | 2 584 398 | 1/1987 |
| WO | WO 2013/115889 | 8/2013 |

OTHER PUBLICATIONS

Atkinson et al., *Syntheses of the alkali metal borodeuterids*, Canadian J. of Chem. vol. 45, 1967.
Colombier, et al., *Studies of the Pyrolysis of Tetraethylammonium Tetrahydroborate*, Inorganica Chimica Acta, 115 (1986) 11-16.
Adams et al., *A New Synthetic Route to Boron-10 Enriched Pentaborane(9) from Boric Acid and Its Conversion to anti-$^{10}B_{18}H_{22}$*, J.Am. Chem. Soc., vol. 124, No. 25, pp. 7292-7293, 2002.
Sivaev, et al., *Chemistry of closo-Dodecaborate Anion $[B_{12}H_{12}]^{2-}$: A Review*, Collection of Czechoslovak Chemical Comm 67(6) (2002) 679-727.
International Search Report and Written Opinion dated May 7, 2015 issued for priority PCT/US2015/14234 filed on Feb. 3, 2015 (8 pgs).
International Search Report and Written Opinion dated Apr. 23, 2015 issued for priority PCT/US2015/14224 filed on Feb. 3, 2015 (11 pgs).
Supplementary European Search Report dated Sep. 7, 2017 for corresponding EP 3102586 filed on Feb. 3, 2015 (8 pgs).
Database WPI, Abstract, Week 201434, Thomson Scientific, London, GB; AN 2014-K04555 & CN 103694267A; XP002772985, Apr. 2, 2014. (2 pgs).
Mongeot, H. et al., Article, "(Et4N)2B10H10 et (Et4N)2B12H12: synthese de Et4NBH4 , separation et purification", Bulletin de la Societe Chimique de France, Societe Francaise de Chimie, Paris, France, vol. 3 (Jan. 1, 1986), pp. 385-389. (6 pgs) (Text of Article is in French).

* cited by examiner

*Primary Examiner* — Amber R Orlando
*Assistant Examiner* — Syed T Iqbal
(74) *Attorney, Agent, or Firm* — Stinson Leonard Street LLP

(57) ABSTRACT

The present invention is directed to a process for the synthesis of alkali metal tetrahydroborates-$^{10}$B and amine borane-$^{10}$B precursors, such as sodium tetrahydroborate-$^{10}$B and triethylamine borane-$^{10}$B.

27 Claims, No Drawings

SYNTHESIS OF BORANE COMPOUNDS

CROSS-REFERENCE TO RELATED APPLICATIONS

This application is based on and claims priority to U.S. Provisional Application Ser. No. 61/965,689 filed on Feb. 3, 2014, which is hereby incorporated herein by reference.

BACKGROUND OF THE INVENTION

1. Field of the Invention

The present invention relates in general to a method for the synthesis of alkali metal tetrahydroborates-$^{10}$B as well as a precursor amine borane-$^{10}$B, such as triethylamine borane -$^{10}$B.

2. Description of Related Art

Isotopically enriched alkali metal tetrahydroborates-$^{10}$B (M$^{10}$B$_4$, M=Li, Na, K, Cs) are commercially unavailable compounds which are used in research laboratories for the preparation of therapeutic agents for the boron neutron capture therapy of cancer (BNCT). Because of the high $^{10}$B nuclei content it can also be used for the synthesis of materials with neutron-absorbing properties.

There are known methods for the synthesis of alkali metal tetrahydroborates-$^{10}$B. However, known methods rely upon expensive chemicals, some of which are not readily available, utilize high temperatures, and/or are not easily scaled for industrial applications.

BRIEF SUMMARY OF THE INVENTION

In one aspect, the present invention is directed to a process for the synthesis of alkali metal tetrahydroborates-$^{10}$B and includes the steps of first, reacting $^{10}$B-enriched boric acid with a $C_2$-$C_4$ alcohol in a reaction mixture that does not include toluene, xylene, mesitylene, benzene, or 1,2-dichlorhoethane to produce trialklylborate-$^{10}$B; second, reacting the trialklylborate-$^{10}$B with a metal aluminum hydride in the presence of an amine to produce amine borane-$^{10}$B; and third, reacting the amine borane-$^{10}$B with a reagent selected from the group consisting of alkali metal hydrides and alkali metal methoxides to produce alkali metal tetrahydroborates-$^{10}$B.

In one embodiment, the first reacting step utilizes a $C_2$-$C_4$ alcohol selected from the group consisting of 1-butanol, ethanol, 2-propanol, or 2-butanol to produce tributylborate-$^{10}$B, triethylborate-$^{10}$B, and tripropylborate-$^{10}$B.

In yet another embodiment, excess alcohol produced during the first reacting step may be separated from the reaction mixture by distillation and reused in the first reacting step.

In one embodiment, the second reacting step utilizes a solvent, which may be a linear or cyclic ether, such as diethyl ether, tetrahydrofuran (THF), 1,4-dioxane, dimethoxyethane (DME) or diglyme. In such an embodiment, the second reacting step may include the following steps: 1) forming a mixture of the amine, the metal aluminum hydride, and the solvent, 2) adding the trialkylborate-$^{10}$B dropwise to the mixture to form a second mixture; and 3) allowing the second mixture to warm to room temperature.

In certain embodiments, the second reacting step utilizes a metal aluminum hydride such as lithium aluminum hydride, sodium aluminum hydride, or potassium aluminum hydride. In certain embodiments, the amine used in the second step is selected from the group consisting of tertiary amines, pyridines and dialkylanilines. The second reacting step produces a solution that includes amine borane-$^{10}$B, a product that may be separated by filtration. Excess solvent present following the second reacting step may be separated from the solution by distillation and reused in the second reacting step.

In one embodiment, the third reacting step utilizes an alkane solvent, which may be a high-boiling linear or cyclic alkane, such as decalin, undecane, dodecane, tridecane, tetradecane, pentadecane or hexadecane. In certain embodiments, the alkali metal of the alkali metal hydride or alkali metal methoxide may be lithium, sodium, potassium or cesium. In certain embodiments, the third reaction step produces a suspension that includes alkali metal tetrahydroborate-$^{10}$B, a product that may be separated from the reaction mixture by filtration. Excess solvent from the third reaction step may be separated from the solution by distillation and reused in the third reacting step. In certain embodiments, the third reacting step produces trimethylborate-$^{10}$B and/or triethylamine, products that may be separated by distillation and reused during the second reaction step. The trimethylborate-$^{10}$B may be separated from triethylamine by further distillation.

In certain embodiments, the trialkylborate-$^{10}$B is tributylborate-$^{10}$B, the amine is triethylamine borane-$^{10}$B and/or the alkali metal is sodium.

In certain embodiments the present invention is directed to a process for the synthesis of amine borane-$^{10}$B and includes the step of reacting trialkylborate-$^{10}$B with a metal aluminum hydride in the presence of an amine, which may be selected from the group consisting of tertiary amines, pyridines and dialkylanilines. In certain embodiments the metal aluminum hydride is lithium aluminum hydride, sodium aluminum hydride, or potassium aluminum hydride. In certain embodiments, the trialkylborate-$^{10}$B is selected from the group consisting of tributylborate-$^{10}$B and trimethylborate-$^{10}$B. The trialkylborate-$^{10}$B may be produced using a trialkylborate-$^{10}$B formed by the first reaction step of the present invention. The trialkylborate-$^{10}$B could also be recovered from the third reaction step of the present invention.

In certain embodiments the present invention is directed to a process for the synthesis of an alkali metal tetrahydroborate-$^{10}$B and includes the step of reacting an amine borane-$^{10}$B with a reagent selected from the group consisting of alkali metal hydride and alkali metal methoxide. The amine borane-$^{10}$B may be produced from the second reaction step of the present invention. The amine borane $^{10}$B may be triethylamine borane-$^{10}$B. In certain embodiments the alkali metal is sodium.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed to a process for the synthesis of alkali metal tetrahydroborates-$^{10}$B. The process of the present invention comprises three steps.

In the first step, $^{10}$B-enriched boric acid is reacted with an alcohol to produce trialkylborate-$^{10}$B. The reaction can take place without the use of toluene, xylene, mesitylene, benzene, 1,2-dichlorhoethane or other similar azeotropic water-removal solvents. In certain embodiments, the alcohol is a $C_2$-$C_4$ alcohol such as 1-butanol, 2-butanol, ethanol, or 2-propanol and the reaction produces tributylborate-$^{10}$B, triethylborate-$^{10}$B, and tripropylborate-$^{10}$B.

In the second step, trialkylborate-$^{10}$B is reacted with a metal aluminum hydride, such as lithium aluminum hydride, sodium aluminum hydride, or potassium aluminum hydride, in the presence of an amine, such as a tertiary amine, a pyridine, or a dialkylaniline to produce an amine borane-$^{10}$B. In certain embodiments the amine is triethylamine, a tertiary amine, and the product of the second step is triethylamine borane-$^{10}$B.

In the third step, the amine borane-$^{10}$B is reacted with an alkali metal hydride or alkali metal methoxide, to produce alkali metal tetrahydroborate-$^{10}$B. In certain embodiments, the alkali metal may be lithium, sodium, potassium or cesium.

The process of the present invention provides a number of benefits. With respect to the first reaction step, it was found that the excess alcohol can act as a solvent for azeotropic water removal. This eliminates the need for traditional azeotropic water removal solvents such as toluene and benzene used in prior art methods for synthesizing, for example, tributylborate-$^{10}$B from $^{10}$B-enriched boric acid. Use of an alcohol as both a reagent and the solvent also facilitates product isolation, allowing high yield of product, preferably over 80%. Further, the alcohol can easily be separated from the water in the distillate, regenerated and reused in the synthesis process.

The process of the present invention incorporates intermediate second and third reaction steps. The second reaction step is carried out under mild conditions, using inexpensive and readily available reagents, and is complete in a relatively short period of time, usually 30 minutes from the addition of trialkylborate-$^{10}$B. The amine borane-$^{10}$B intermediates are extremely stable to hydrolysis and therefore do not require special storage conditions.

With respect to both the second and third reaction steps, the amine borane-$^{10}$B and the alkali metal tetrahydroborate-$^{10}$B can be separated by simple filtration and evaporation of the volatiles. These reaction steps also allow the solvents from the second and third steps, as well certain reagents, to be redistilled and reused. The processes of the present invention utilize inexpensive reagents, moderate temperatures, and can be easily scaled up for industrial applications.

Certain exemplary embodiments are described in more detail as follows:

Step One: Synthesis of trialkylborate-$^{10}$B

In the first step, $^{10}$B-enriched boric acid and an alcohol such as 1-butanol, ethanol, 2-propanol, or 2-butanol are reacted to produce trialkylborate-$^{10}$B. $^{10}$B-enriched boric acid and the alcohol are first placed in a reaction vessel and thoroughly mixed. Attached to the reaction vessel is an azeotropic or regular distillation device. The reaction is preferably carried out in an inert atmosphere such as argon or nitrogen gas to avoid unwanted side reactions with moisture. The molar ratio of $^{10}$B-enriched boric acid to alcohol is preferably between 1:2.9 and 1:3.1 and in certain embodiments is 1:3. The reaction mixture is then heated to reflux. During the reaction, water is produced as a byproduct and is separated from the reactor by the azeotropic or regular distillation device. The alcohol acts as both a reagent and as a solvent for the azeotropic removal of water as the reaction proceeds. The trialkylborate-$^{10}$B is then separated from the excess alcohol using a distillation device. The reaction and distillation are carried out at temperatures appropriate for the alcohol used, as will be readily understood by one of ordinary skill in the art.

In the embodiment discussed herein, the alcohol is 1-butanol and the product is tributylborate-$^{10}$B. The reaction mixture is heated to reflux until it reaches a temperature preferably of at least 117° C., more preferably between 125° C. and 135° C., and in certain embodiments about 130° C. The tributylborate-$^{10}$B is separated from the excess alcohol using a distillation device, and the distillation proceeds until the temperature of the reaction mixture reaches at least 200° C., more preferably between 220 and 240° C., and in certain embodiments between 220-230° C.

The use of alcohol makes it unnecessary to add toluene, xylene, mesitylene, benzene, or 1,2-dichlorhoethane. Additionally, the excess distilled alcohol can be recovered, separated from any residual water via distillation, and reused in a subsequent synthesis reaction.

Step Two: Synthesis of amine borane-$^{10}$B

In the second step, trialkylborate-$^{10}$B is reacted with a metal aluminum hydride such as lithium aluminum hydride, sodium aluminum hydride, or potassium aluminum hydride, in the presence of an amine, such as a tertiary amine, a pyridine, or a dialkylaniline to produce an amine borane-$^{10}$B. Preferably, the reaction is carried out using a solvent, which may be a linear or cyclic ether, such as diethyl ether, tetrahydrofuran (THF), 1,4-dioxane, dimethoxyethane (DME), or diglyme.

The amine is first added to a suspension of metal aluminum hydride in the solvent. The molar ratio of the amine to the metal aluminum hydride is preferably between 1.25:1 and 1.35:1, and in certain embodiments 1.3:1. The resulting mixture is then cooled to a temperature preferably ranging from 5° C. to 15° C., and in certain embodiments about 10° C. Trialklylborate-10B is subsequently added dropwise to the reaction mixture for a time preferably ranging from 0.5 to 2 minutes, more preferably ranging from 1 to 1.5 minutes, and in certain embodiments 10-15 minutes or more, depending on the reaction scale, with constant stirring. The molar ratio of the total amount of trialkylborate-$^{10}$B added to the reaction mixture to the metal aluminum hydride is preferably between 1:1.25 and 1:1.35, and in certain embodiments 1:1.1 to 1:1.4.

The reaction mixture is then allowed to warm up to room temperature with constant stirring for at least 20 minutes and in some embodiments 30 minutes. The resulting solution of amine borane-$^{10}$B is then preferably filtered from the precipitate and the precipitate is washed with ether, or another solvent, which may be a linear or cyclic ether. The amine borane-$^{10}$B solution may be washed with water or an aqueous NaCl solution, dried in the presence of a drying agent including but not limited to sodium sulfate, calcium chloride, calcium sulfate, or magnesium sulfate, filtered and finally isolated via evaporation of the solvent.

The evaporated solvent can be distilled and reused in the second reaction step. In one embodiment discussed herein, the starting material of the second step is tributylborate-$^{10}$B, the amine is triethylamine and the product is triethylamine borane-$^{10}$B. However, other trialkylborates and amines of the type disclosed herein can be used to produce other amine borane-$^{10}$B compounds consistent with the present invention. The synthesis of triethylamine borane-$^{10}$B is usually complete within thirty minutes after all of the tributylborate-$^{10}$B is added.

Step Three: Synthesis of alkali metal tetrahydroborate-$^{10}$B

In certain embodiments, alkali metal tetrahydroborate-$^{10}$B may be synthesized from the reaction of an amine borane-$^{10}$B with alkali metal hydride. In certain other embodiments, alkali metal tetrahydroborate-$^{10}$B is synthesized from the reaction of amine borane-$^{10}$B with alkali metal methoxide. In one embodiment discussed herein, the amine borane-$^{10}$B is triethylamine borane.

Alkali Metal Hydride Reaction

In certain embodiments of the third step, alkali metal hydride may be reacted with amine borane-$^{10}$B to produce alkali metal tetrahydroborate-$^{10}$B. The reaction is an addition reaction of alkali metal hydride to the [$^{10}$BH$_3$] fragment with the displacement of the amine from the complex. The alkali metal hydride is reacted with amine borane-$^{10}$B in a reaction vessel. The alkali metal hydride is preferably provided as a dispersion in mineral oil to prevent it from igniting in air. The reaction is preferably carried out in an inert atmosphere such as argon or nitrogen gas, to prevent alkali metal hydride from reacting with air. The molar ratio of amine borane-$^{10}$B to alkali metal hydride is preferably 0.95:1 and 1.05:1, and in some embodiments about 1:1. A solvent, which may be a high boiling linear or cyclic alkane solvent, such as decalin, undecane, dodecane, tridecane, tetradecane, pentadecane, or hexadecane is preferably added to the reaction vessel to serve as a reaction solvent. In certain embodiments, the solvent is not diglyme. The ratio of the solvent to sodium hydride dispersion should be around 10 mL per 1 gram.

The resulting mixture is then heated until it reaches a desired temperature and held at that temperature range, in some embodiments for at least 1.5 hours, and in some embodiments for two hours. During this reaction, amine by-products, as well as excess solvent, are distilled off from the reaction vessel. The reaction progress can be monitored by tracking the rate of distillation of the amine by product, which can be collected and reused in the second reacting step.

The reaction mixture is then allowed to cool to room temperature at which point the alkali metal tetrahydroborate-$^{10}$B may be filtered. In certain embodiments, the filtration occurs at temperatures lower than 10° C. The resulting precipitate is then preferably washed with a solvent, which in certain embodiments may be hexane, pentane or a linear or cyclic ether to remove mineral oil or excess solvent. The precipitate is also preferably, but not necessarily, washed with a solvent, such as 2-propanol or a tertiary butanol, in order to remove residual sodium hydride. Finally, the precipitate is dried. Suitable temperatures for each aspect of third step can be readily determined by one of ordinary skill in the art.

In one embodiment discussed herein, the amine borane-$^{10}$B is triethylamine borane $^{10}$B, the alkali metal hydride is sodium hydride, and the alkali metal tetrahydroborate-$^{10}$B is sodium tetrahydroborate-$^{10}$B. The sodium hydride is preferably provided as a 60% w/w dispersion in mineral oil given to prevent it from igniting in air. The resulting mixture is then heated until it reaches a temperature of at least 120° C., and in certain embodiments between about 130-150° C., and held at that temperature range for at least 1.5 hours, and in some embodiments for two hours. During this reaction, the triethylamine produced as well as excess solvent is distilled off from the reaction vessel. The reaction progress can be monitored by tracking the rate of distillation of the triethylamine, which can be collected and reused in the second reacting step.

The reaction mixture is then allowed to cool to room temperature at which point the sodium tetrahydroborate-$^{10}$B may be filtered, given that sodium tetrahydroborate-$^{10}$B is not soluble in the solvent. The resulting precipitate is then preferably washed with a solvent, which in certain embodiments may be hexane, pentane or a linear or cyclic ether to remove mineral oil or excess solvent. The precipitate is also preferably, but not necessarily, washed with a solvent, such as 2-propanol or a tertiary butanol, in order to remove residual sodium hydride. Finally, the precipitate is dried.

Alkali Metal Methoxide Reaction

In certain embodiments, the third step proceeds via a reaction between amine borane-$^{10}$B and alkali metal methoxide in an alkane solvent. The alkali metal methoxide, amine borane-$^{10}$B, and the solvent, which may be a high boiling linear or alkane solvent, such as decalin, undecane, dodecane, tridecane, tetradecane, pentadecane or hexadecane, are placed in a reaction vessel. In certain embodiments, the solvent is not diglyme. By "high boiling" solvent, the boiling point of the solvent is preferably at least 180° C. and in some embodiments at least 187° C.

The molar ratio of amine borane-$^{10}$B to alkali metal methoxide is preferably between 1.25:1 and 1.35:1 and in certain embodiments is 1.3:1. The resulting mixture is stirred and heated. As the reaction mixture is heated and the reaction proceeds, amine and trialkylborate-$^{10}$B are distilled off. The reaction mixture is then cooled to room temperature. The reaction mixture is preferably diluted by diethyl ether, pentane, hexane or another linear or cyclic ether and filtered. The filtrate is then washed, which wash may be conducted using ether, penthane, hexane, tetrahyrofurane, dioxane or dimethoxyethane, and dried. The solvent in the supernatant may be separated and reused.

In one embodiment discussed herein, the amine borane-$^{10}$B is triethylamine borane $^{10}$B, the alkali metal methoxide is sodium methoxide, and the alkali metal tetrahydroborate-$^{10}$B is sodium tetrahydroborate-$^{10}$B. The molar ratio of triethylamine borane-$^{10}$B to sodium methoxide is preferably between 1.25:1 and 1.35:1 and in certain embodiments is 1.3:1. The resulting mixture is stirred and heated to a temperature of at least 150-160° C., and in certain embodiments about 180° C. As the reaction mixture is heated to 120-130° C. and the reaction proceeds, triethylamine and trimethylborate-$^{10}$B are distilled off The reaction mixture is then cooled to room temperature. The reaction mixture is preferably diluted by diethyl ether, pentane, hexane or another linear or cyclic ether and filtered. The filtrate is then washed with ether, pentane, hexane, tetrahyrofurane, dioxane or dimethoxyethane and dried. The solvent in the supernatant may be separated and reused.

In both processes discussed above, amines, such as triethylamine, produced during the reaction may be separated by distillation and reused in the second reaction step. In the alkali metal methoxide reaction, distilled amines, such as triethylamine, and trialkylborate-$^{10}$B, such as trimethylborate-$^{10}$B can be separated via further distillation (b.p. $^{10}$B (OMe)$_3$ 68-69°, b.p. Et$_3$N 89° C.) and reused in the process of the present invention. Likewise, the trimethylborate-$^{10}$B can be separated by distillation from triethylamine and used in the second reaction step instead, or in combination with, trialkylborate-$^{10}$B produced in step one.

EXAMPLES

The three-step synthesis of sodium tetrahydroborate-$^{10}$B is demonstrated with the following two exemplary and non-limiting examples.

Example 1

Step 1. Synthesis of tributylborate-$^{10}$B

In a 3 L 3-necked round-bottom flask equipped with an overhead stirrer, thermometer/argon inlet adapter with a stopcock, and a Dean-Stark trap was placed $^{10}$B-enriched boric acid (Boron Products LLC, 95% $^{10}$B enrichment, 1250 g, 4.01 mol) and 1-butanol (Fisher Scientific, ACS-grade, 2100 mL). The reaction mixture was heated to reflux during 3 h, until the temperature in the reaction mixture reached 130° C. and about ⅔ of the theoretical amount of water was collected in the trap. In a stream of argon, the Dean-Stark trap was changed to a distillation head and the leftover 1-butanol was distilled off until the temperature of the reaction mixture reached 220-230° C. The product was then collected as a clear colorless liquid (bp 230-232° C./760 mm Hg, 846.5 g, 90%). The product was characterized by a combination of $^1$H, $^{10}$B, and $^{13}$C$\{^1$H$\}$ NMR spectra.

Step 2. Synthesis of triethylamine borane-$^{10}$B

Anhydrous triethylamine (15.3 mL, 0.11 mol) was added to a suspension of 95% lithium aluminum hydride (3.20 g. 0.08 mol) in anhydrous diethyl ether (70 mL), and the resulting mixture was cooled to 10° C. on an ice-bath. Tributylborate-$^{10}$B (22.9 g, 0.10 mol) was added dropwise to the reaction mixture during 10-15 minutes under constant stirring. The reaction mixture formed was allowed to warm to room temperature and was stirred for 30 minutes. The precipitate was filtered on air using a coarse porosity glass frit and then was washed with ether (30 mL). Ethereal layers were combined, washed with 13% wt aqueous NaCl, dried over sodium sulfate, filtered and evaporated to give the product as a clear colorless liquid (10.3 g, 90%). The product was characterized by a combination of $^1$H, $^{10}$B, and $^{13}$C$\{^1$H$\}$ NMR spectra.

Step 3. Synthesis of sodium tetrahydroborate-$^{10}$B

In a 100 mL 3-necked round-bottom flask equipped with an overhead stirrer, thermometer/argon inlet adapter with a stop cock, and a distillation head was placed sodium hydride (60% dispersion in mineral oil, 3.61 g, 90.3 mmol), triethylamineborane-$^{10}$B (10.3 g, 90.3 mmol), and anhydrous decalin (36 mL). The resulting mixture was heated until the distillation of triethylamine started (internal temperature 130-150° C.), and then was kept at 150° C. for 2 hours. The reaction mixture was allowed to cool to room temperature and was filtered on a medium-porosity glass frit. The precipitate was washed with hexane (20 mL), 2-propanol (5 mL), and dried under the vacuum of an oil pump to give the target compound as a white powder (2.98 g, 89%). The product was characterized by a combination of $^1$H, $^{10}$B, and $^{13}$C$\{^1$H$\}$ NMR spectra.

Example 2

Step 1. Synthesis of tributylborate-$^{10}$B

In a 5 L 2-necked round-bottom flask equipped with a thermometer/argon inlet adapter, a distillation setup (distillation adapter, thermometer, condenser, receiver adapter, and a 2 L round-bottom flask), and a heating mantle several was placed $^{10}$B-enriched boric acid (Boron Products LLC, 95% $^{10}$B enrichment, 450 g, 7.38 mol), 1-butanol (Fisher Scientific, ACS-grade, 4100 mL), and several boiling stones. The reaction mixture was heated on a heating mantle in a slow stream of argon until distillation started (internal temperature 100-120° C., distillation temperature 98-112° C.) and continued until the 2 L receiver was full (complete azeotropic distillation of water-1-butanol mixture). After the temperature of the reaction mixture reached 130° C., the receiver was changed to a 0.5 L round-bottom flask, and excess 1-butanol (b.p. 117-118° C.) was distilled off. The temperature of the reaction mixture was then slowly increased to 235-245° 1 C. until the product (b.p. 228-230° C.) started distilling. After first several milliliters of the product, the distillation was stopped and the reaction mixture was allowed to cool down to room temperature in a stream of argon. The distillation flask contained pure product as determined by a combination of $^1$H, $^{10}$B, and $^{13}$C$\{^1$H$\}$ NMR spectra (see attachment). The product is a moisture-sensitive clear colorless liquid (1530-1630 g, 90-96%).

Step 2. Synthesis of triethylamine borane-$^{10}$B

Anhydrous triethylamine (15.3 mL, 0.11 mol) was added to a suspension of 95% lithium aluminum hydride (3.20 g, 0.08 mol) in an anhydrous diethyl ether (70 mL), and the resulting mixture was cooled to 10° C. on an ice-bath. Tributylborate-$^{10}$B (22.9 g, 0.10 mol) was added dropwise to the reaction mixture during 10-15 minutes under constant stirring. The reaction mixture formed was allowed to warm to room temperature and was stirred for 30 min. The precipitate was filtered on air using a coarse porosity glass fit and then was washed with ether (30 mL). Ethereal layers were combined and evaporated to give the product as a clear colorless liquid (10.3 g, 90%). The product was characterized by a combination of $^1$H, $^{10}$B, $^{10}$B$\{^1$H$\}$ NMR spectra (see attachment). The reaction was scaled up in a 6 L glass apparatus using 750 mL (2.78 mol) of tributylborate-$^{10}$B, 84 g of 95% lithium aluminum hydride (2.21 mol), and 427 mL (3.07 mol) of 99% triethylamine in 3 L of diethyl ether (anhydrous, stabilized, ACS-certified). Addition times were increased to 1-1.5 h and the reaction time was increased to 1-1.5 h. The reaction mixture was filtered and evaporated. Yields of the product ranged from 222 g to 270 g (70-85%).

Step 3. Synthesis of sodium tetrahydroborate-$^{10}$B

Sodium Hydride Reaction

In a 100 mL 3-necked round-bottom flask equipped with an overhead stirrer, thermometer/argon inlet adapter with a stopcock, and a distillation head was placed sodium hydride (60% dispersion in mineral oil, 3.61 g, 90.3 mmol), triethylamine borane-$^{10}$B (10.3 g, 90.3 mmol), and anhydrous decalin (36 mL). The resulting mixture was heated until the distillation of triethylamine started (internal temperature 130-150° C.), and then was kept at 150° C. for 2 h. The reaction mixture was allowed to cool to room temperature and was filtered on a medium-porosity glass frit. The precipitate was washed with hexane (20 mL), 2-propanol (5 mL), and dried under vacuum of an oil pump to give the target compound as a white powder (2.98 g, 89%). The product was characterized by a combination of $^1$H, $^{10}$B, and $^{10}$B$\{^1$H$\}$ NMR spectra (see attachment).

Sodium Methoxide Reaction

In a 3 L 3-necked round-bottom flask equipped with an overhead stirrer, a thermometer adapter with argon inlet, and a distillation system (distillation adapter, thermometer, condenser connected to a recirculating chiller kept at 0° C., and a 1 L receiving flask) was placed sodium methoxide (162 g, 3.0 mol), triethylamine borane-$^{10}$B (586 mL, 4 mol), and decalin (800 mL) Upon vigorous stirring, the reaction mixture was slowly heated to 180° C. After the reaction mixture reached 120-130° C., distillation of triethylamine and trimethylborate-$^{10}$B started (total ~550-600 g of distillate). The distillation was complete after the reaction temperature reached 150-160° C. After cooling to room temperature, the reaction mixture was diluted with 0.5 L of diethyl ether and filtered. The filtrate was washed with 300 mL of ether and dried in a vacuum oven at 140° C. during 2 h. Product ($Na^{10}BH_4$) is a white powder (87-106 g, 87-95%). The product was characterized by a combination of $^1H$, $^{10}B$, and $^{10}B\{^1H\}$ NMR spectra.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. A process for the synthesis of alkali metal tetrahydroborates comprising the following steps:
   first, reacting $^{10}B$-enriched boric acid with a $C_2$-$C_4$ alcohol in a reaction mixture that does not include toluene, xylene, mesitylene, benzene, or 1,2-dichlorhoethane to produce trialkylborate-$^{10}B$;
   second, reacting the trialkylborate-$^{10}B$ with a metal aluminum hydride in the presence of an amine to produce amine borane-$^{10}B$; and
   third, reacting the amine borane-$^{10}B$ with a reagent selected from the group consisting of alkali metal hydride and alkali metal methoxide to produce alkali metal tetrahydroborate-$^{10}B$.

2. The process of claim 1, wherein the second reacting step utilizes a linear or cyclic ether solvent.

3. The process of claim 2, wherein the linear or cyclic ether solvent is selected from the group consisting of diethyl ether, tetrahydrofuran (THF), 1,4-dioxane, dimethoxyethane (DME), diglyme.

4. The process of claim 1, wherein the third reacting step utilizes a linear or cyclic alkane solvent.

5. The process of claim 4, wherein the linear or cyclic alkane solvent is selected from the group consisting of decalin, undecane, dodecane, tridecane, tetradecane, pentadecane, hexadecane.

6. The process of claim 1, wherein the $C_2$-$C_4$ alcohol selected from the group consisting of 1-butanol, ethanol, 2-propanol, and 2-butanol.

7. The process of claim 1, wherein the alkali metal is selected from the group consisting of lithium, sodium, potassium and cesium.

8. The process of claim 1, wherein the amine is selected from the group consisting of a tertiary amine, a pyridine or a dialkylaniline.

9. The process of claim 1, wherein the metal aluminum hydride is selected from the group consisting of lithium aluminum hydride, sodium aluminum hydride, and potassium aluminum hydride.

10. The process of claim 2, wherein the second reacting step comprises:
    forming a mixture of said amine, said metal aluminum hydride, and said solvent;
    cooling the mixture;
    adding said trialkylborate-$^{10}B$ dropwise to said mixture to form a second mixture; and
    allowing said second mixture to warm to room temperature.

11. The process of claim 1, wherein the second reacting step produces a solution comprising said amine borane-$^{10}B$ and said amine borane-$^{10}B$ is separated from the precipitate by filtration.

12. The process of claim 2, wherein excess solvent from said second reacting step is separated from the solution and reused in said second reacting step by distillation.

13. The process of claim 1, wherein the third reacting step produces a suspension comprising said alkali metal tetrahydroborate-$^{10}B$ and said alkali metal tetrahydroborate-$^{10}B$ is separated from the suspension by filtration.

14. The process of claim 4, wherein excess solvent from said third reacting step is separated from the solution by distillation and reused in said third reacting step.

15. The process of claim 1, wherein after said first reacting step excess alcohol is separated from the reaction mixture by distillation and reused in said first reacting step.

16. The process of claim 1, wherein said third reacting step produces amine, the amine is separated from the reaction mixture by distillation, and the amine is reused in said second reacting step.

17. The process of claim 1, wherein said third reacting step produces trimethylborate-$^{10}B$, the trimethylborate-$^{10}B$ is separated from the reaction mixture by distillation, and the trimethylborate-$^{10}B$ is reused in said second reacting step.

18. The process of claim 1, wherein said third reacting step produces trimethylborate-$^{10}B$ and amine, the trimethylborate-$^{10}B$ and amine are separated from said reaction mixture by distillation during the third reaction step to form a distillate comprising the trimethylborate-$^{10}B$ and amine, and the trimethylborate-$^{10}B$ is separated from amine in the distillate by further distillation.

19. The process of claim 9, wherein the metal aluminum hydride is lithium aluminum hydride and the $C_2$-$C_4$ alcohol is 1-butanol.

20. A process for the synthesis of an amine borane-$^{10}B$ comprising the step of reacting trialkylborate-$^{10}B$ with a metal aluminum hydride in the presence of an amine selected from the group consisting of a tertiary amine, a pyridine or a dialkylaniline.

21. The process of claim 20 wherein the metal aluminum hydride is selected from the group consisting of lithium aluminum hydride, sodium aluminum hydride, or potassium aluminum hydride.

22. The process of claim 20, wherein the trialkylborate-$^{10}B$ is selected from the group consisting of tributylborate-$^{10}B$ and trimethylborate-$^{10}B$.

23. The process of claim 20, wherein the amine is triethylamine.

24. The process of claim 20, wherein the metal aluminum hydride is lithium aluminum hydride and the $C_2$-$C_4$ alcohol is 1-butanol.

25. A process for the synthesis of alkali metal tetrahydroborate-$^{10}B$ comprising the step of reacting amine borane-$^{10}B$ with a reagent selected from the group consisting of alkali metal hydride and alkali metal methoxide.

26. The process of claim 25, wherein the amine borane-$^{10}B$ is triethylamine borane-$^{10}B$.

27. The process of claim 25, further comprising adding a linear or acyclic alkane solvent.

* * * * *